United States Patent [19]

Kalka et al.

[11] 4,056,981

[45] Nov. 8, 1977

[54] PROCESS AND APPARATUS FOR WITHDRAWING A SAMPLE FROM A REACTION VESSEL UNDER PRESSURE

[75] Inventors: Josef Kalka, Herten; Walter Waskönig; Karl Lueg, both of Marl, all of Germany

[73] Assignee: Chemische Werke Huls Aktiengesellschaft, Marl, Germany

[21] Appl. No.: 767,422

[22] Filed: Feb. 10, 1977

[30] Foreign Application Priority Data

Feb. 19, 1976 Germany .............................. 2606687

[51] Int. Cl.² .............................................. G01N 1/14
[52] U.S. Cl. .................................................. 73/421 B
[58] Field of Search ........... 73/421 B, 422 GC, 425.6, 73/425.4 R, 422 R; 23/259

[56] References Cited

U.S. PATENT DOCUMENTS

| | | | |
|---|---|---|---|
| 3,229,711 | 1/1966 | Leopold et al. ........................ | 73/422 |
| 3,298,236 | 1/1967 | Thomas ................................ | 73/425.6 |
| 3,776,042 | 12/1973 | Werra ................................... | 73/421 B |
| 3,952,729 | 4/1976 | Libman ................................ | 73/425.6 |
| 4,010,648 | 3/1977 | Harris et al. ........................ | 73/425.4 |

*Primary Examiner*—S. Clement Swisher
*Attorney, Agent, or Firm*—Millen & White

[57] ABSTRACT

A process and apparatus for the withdrawal of samples from a reaction vessel under pressure containing a solid-liquid dispersion, emulsion, or suspension sensitive to mechanical stress, wherein a portion of the liquid consists of a liquefied gas present in the emulsion, dispersion, or suspension in a dissolved or emulsified form, as for example, the withdrawal of samples during the manufacture of polyvinyl chloride in accordance with the suspension or emulsion method. A syringe and cannula combination are filled with an inert protective fluid with the cannula being passed through a valve arrangement in the reaction vessel to eject the protective fluid thereinto and to replace the ejected fluid with a sample from the reaction vessel. The sample-containing syringe is sealed before withdrawal of the cannula of the combination from the reaction vessel, which is again sealed by the valve arrangement.

10 Claims, 1 Drawing Figure

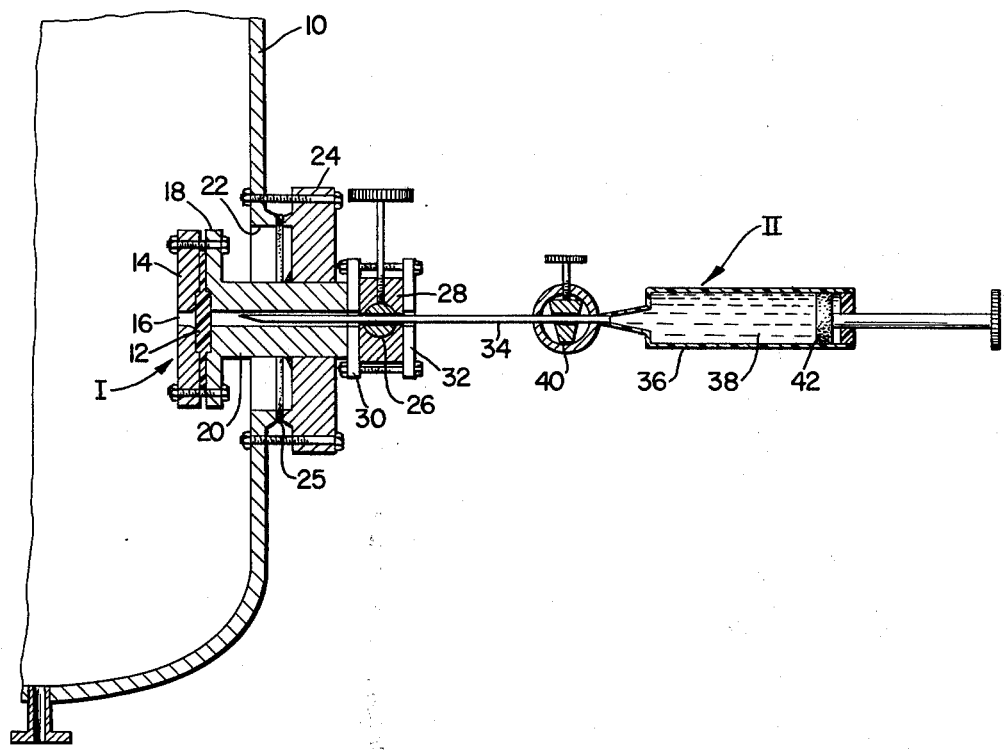

PROCESS AND APPARATUS FOR WITHDRAWING A SAMPLE FROM A REACTION VESSEL UNDER PRESSURE

BACKGROUND OF THE INVENTION

Methods for the withdrawal of samples from liquid, powders, and gases have been known for a long time. The siphon procedure in various modifications is suitable for the simple sample withdrawal from liquids and solutions. The same method is also applicable to stable suspensions, dispersions, and emulsions. In contrast thereto, if mixtures of liquids with readily volatile compounds are involved, samples are withdrawn by way of valving arrangements, such as gate valves, etc., in a multistage procedure. A compilation of the most well-known methods can be found in Kolthoff: "Treatise on Analytical Chemistry, Part I, Volume I," pp. 81 et esq.

When taking samples from dispersions and/or emulsions under pressure, which are highly sensitive to mechanical stress as well as to pressure expansion, as they are formed, for example, in the emulsion polymerization of vinyl chloride, the method heretofore employed has been discharging, via valves, a very large amount of sample in a multistage operation as the only possible way of obtaining a representative sample. However, this method is likewise unsatisfactory, since in case of sensitive dispersions, the latter frequently become unstable in the valves and/or in the valve cocks in the sample-withdrawal device, thus clogging the valves. In such a case, it is then no longer possible to obtain additional samples. Furthermore, an exact determination of the content of the dissolved and/or emulsified, gaseous proportion is impossible when following the gate or charging valve procedure, since a partial phase separation into liquid and gas occurs before the final discharge of the sample through the valves. Still further, the gate valve method has the disadvantage that rather large amounts of samples must be withdrawn, since connecting conduits and valves must possess specific and usually large inside cross sections, so that high flow velocities and the attendant instability of the dispersion can be avoided. However, excessive quantities of a sample mean, in any case, a loss of material and, on the other hand, the operating personnel can be inconvenienced and/or endangered thereby, especially when vinyl-chloride-containing samples are involved.

Consequently, the present invention is concerned with a sample withdrawal system which avoids the aforedescribed disadvantages of the prior state of the art.

SUMMARY OF THE INVENTION

According to this invention, there is provided a process and apparatus for the withdrawal of a sample from a reaction vessel under pressure containing a dissolved and/or emulsified solid-liquid dispersion which contains liquefied gas and is sensitive to mechanical stress, wherein the cannula of a pressure-proof injection syringe combination, filled with an inert protective fluid and with permissive sealing at the point where the cannula is attached, is pushed through an elastic, pressure-proof diaphragm provided in the wall of the reaction vessel into the latter; then the protective fluid is injected from the injection syringe into the reaction vessel; subsequently the injection syringe is gradually filled with the solid-liquid dispersion; and then the injection syringe is sealed before the cannula is pulled out of the wall of the reaction vessel. The apparatus for such withdrawal of a sample from a reaction vessel includes a pressure-proof, elastic self-sealing diaphragm arranged in the vessel wall, as well as a pressure-proof injection syringe provided with a needle type cannual, both filled with an inert protective fluid, with the cannula having a length of 5 – 30 cm. and an internal diamter of 1 – 2 mm., which can be used to pierce the diaphragm, and furthermore provided with a shutoff valve at the point where the cannula is attached to the syringe.

DETAILED DISCUSSION

The reaction vessel can be under an ambient pressure of up to about 15 bars, for example, during the polymerization of vinyl chloride. The diaphragm as well as the injection syringe must be able to withstand this pressure. The diaphragm must be capable of being penetrated by the cannula and must be so elastic that it seals off the reaction vessel, after the cannula has been pulled out, safely and without leakage to the outside surroundings. Furthermore, the diaphragm must be able to withstand a large number of penetrations before it has to be exchanged, and the material of which the diaphragm is made must not be susceptible to attack by the substance present in the reaction vessel. A suitable diaphragm material proved to be a vulcanized elastomer, e.g., a rubber on the basis of "PERBUNAN" (neoprene and butadien-acrylonitrile elastomers), ethylene-propylene rubber, or silicone rubber.

To avoid a diaphragm of excessive thickness, diaphragms are suitably employed having an area of 0.2 – 4 $cm^2$. Depending on the strength of the material and the surface area of the diaphragm, a thickness thereof amounting to 2 – 5 mm. is then required. The necessary thickness can be determined from the physical characteristics of the diaphragm material. The diaphragm can be made especially thin and/or more resistant to rupture at any particular thickness, if a diaphragm material is utilized having a layer of a soft rubber and a layer of a harder rubber and/or wherein a soft middle layer is disposed between two harder outer layers. While the harder layer increases the mechanical stability, i.e., rupturing resistance, of the diaphragm, the soft layer ensures a reliable sealing of the diaphragm after penetration by the cannula. The diaphragm can be mounted by means of a flange directly above the opening arranged in the wall of the vessel in which case, the direction of the cannula and syringe can be changed for withdrawing a sample in the event that movement and/or the movement of the dispersion does not carry away the previously ejected protective fluid. However, it is also possible to mount the diaphragm in a separate holder which is in its entirety connected with the vessel wall. For reasons of safety, it is advantageous to arrange a closable valve on the outside in front of the diaphragm, so that in case of leakage or a rupturing of the diaphragm, the discharge of a substance from the reaction vessel can be prevented. The inside cross section or passage of this safety valve, which may be in the form of a ball valve, must be at least so large that the cannula of the injection syringe can be readily passed therethrough. The injection syringe must likewise be pressure-proof and must have a volume sufficient to hold the volume of sample required for the subsequent analytical procedure. In general, 0.1 – 20 cc. is sufficient.

The internal diameter of the cannula, which generally consists of steel or stainless steel, must be larger than the diameter of the particles contained in the dispersion.

Furthermore, in case of a large cannula diameter, the dispersion is not under such a great mechanical stress, since in a larger cannula there is a lower flow velocity and a smaller pressure loss. In case of pressure losses of more than 1 bar, sensitive dispersions already tend to develop manifestations of instability, i.e., they tend to coagulate. However, since in the case of large cannula diameters there is also a large perforation of the diaphragm, increasing the danger to the diaphragm, and since furthermore also the volume of the cannula is increased as compared to the volume of the syringe, thus impairing the accuracy of the analysis, it is advantageous to employ cannulas having an internal diameter of about 0.3 – 2 mm. Such cannulas have an external diameter of about 0.8 – 2.5 mm. The length of the cannula ranges generally between 5 cm. and 30 cm. If the cannula is made longer than 30 cm., the pressure loss in many cases is too high. A length of at least 5 cm. is required, in general, to withdraw a representative sample from the reactor. Under practical conditions, the length of the cannula should be dimensioned so that it projects to an extent of 2 – 20 cm. into the reaction vessel.

The injection syringe is provided, at the point where it is connected with the cannula, with a closable valve which must be closed before the cannula is removed from the reaction vessel, so that the captured sample is not forced out of the syringe by the internal pressure of the dissolved gases. This valve may be of any available type, such as a passaged rotary frusto-conical plug valve, with the passage affording communication between the cannula and syringe in the open position but preventing such communication in the closed position.

To prevent the sample substance from expanding into the cannula and the syringe at the instant of penetration of the diaphragm, resulting in a high mechanical stress, as in mixing, on the dispersion, which leads to a clogging of the cannula, the latter and the syringe are filled with an inert protective fluid. There must be no gas cushions in the cannula and in the syringe. The protective fluid is injected into the mixture to be analyzed after the diaphragm has been penetrated. The protective fluid, therefore, must not exert any influence, either chemically or physically, on the mixture to be analyzed. Suitably, water is utilized as the protective fluid, or preferably water/emulsifier solution corresponding to that utilized in the polymerization. Since the protective fluid is injected into the mixture to be analyzed, the volume of the mixture from which the sample is drawn must be substantially larger than the volume of the protective fluid, so that the thus-produced error is negligible. If this is not the case, the change in the sample composition incurred due to the increase in volume must be taken into account during the analysis.

After the protective fluid has been injected into the sample mixture, a sample is introduced without any bubbles into the syringe by a gradual retraction of the injection syringe plunger. To avoid errors on account of the protective fluid which has remained in the cannula, it may be necessary to rinse the syringe by again injecting the thus-withdrawn sample into the reactor and renewing the sample withdrawal. If there is no motion in the dispersion present in the reaction vessel, by means of which the protective fluid is carried away from the injection point, the sample is taken at some other location of the dispersion by changing the direction of the cannula and syringe. The elastic diaphragm permits such changes in direction. After the sample has been withdrawn into the injection syringe, the valve in the injection syringe is closed and the cannula is pulled out of the diaphragm.

THE DRAWING

The process and apparatus for the sample withdrawal will be explained in greater detail with reference to the accompanying drawing figure.

Mounted in wall 10 of the reaction vessel is a sampling combination I comprising a holder assembly for a diaphragm 12 and consisting of a plate 14, centrally apertured plug 20 by suitable screw, bolt or other fastening means to thus secure the diaphragm 12. Holder assembly I is passed through an opening 22 in wall 10, this opening also permitting removal of the holder assembly for replacement of the diaphragm as may be necessary. This assembly is mounted to the wall of the opening 22 by a mounting support 24 attached to the wall 10 by screw, bolt or other fastening means clamping the support to the wall 10 along an interposed sealing gasket 25. Assembly may assume vatious predetermined positions of adjustment within the vessel relative to the mounting support 24. In case of a possible leakage or a rupturing of the diaphragm, the efflux of material can be prevented by a ball valve 26, mounted on the holder assembly, to be opened before each sample withdrawal and to be closed again after each sample withdrawal. Valve 26 comprises a valve housing 28 secured to a flange 30 on the adjacent end of plug 20 by a flange 32 on the non-adjacent end on housing 28 by screws, bolts or other fastening means.

For the sample withdrawal, the cannula 34 of the injection syringe II, which can consist of glass, a synthetic resin, or metal, is passed through the ball valve aperture and the plug aperture and is made to pierce the diaphragm M. The cannula K and the injection syringe 36 are filled with the protective fluid 38. During the piercing or penetration, the valve 40 of the syringe is suitably closed, but this is not absolutely necessary. After the cannula has pentrated, valve 40 of the syringe, if closed is opened and the protective fluid is forced into the reaction vessel by advancing the plunger 42. If the liquid in the reaction vessel or autoclave is not in motion, a sample is withdrawn from another position by changing the position of cannula and syringe, by carefully allowing the plunger to move backwards under the effect of the pressure ambient in the vessel or autoclave, until an exactly known quantity is contained in the syringe. Suitably, this procedure of withdrawing and reinjection is repeated several times. Once an exactly known quantity is contained in the syringe, the valve 40 is closed to close communication between the syringe and the cannula and the cannula is pulled out of the self-sealing diaphragm 12 and clear of the ball valve 26, which is closed upon complete removal of the cannula. Thus, a representative sample from the reaction vessel is in the injection syringe and can be further analyzed.

The proportion of the readily volatile compounds can be determined, for example, by analyzing the content of the syringe, the column of which is known exactly, directly in a gas chromatograph. Of course, it is also possible to conduct on the sample all other analyses, such as, for example, the determination of the pH value, of the solids content, of the density, and so on.

The process and apparatus of this invention have the advantages that they are very simple, no poisonous gases are liberated during the taking of the sample, only minor amounts are required for a sample, and the thus-withdrawn quantities are constantly controllable during the sample withdrawal step. Furthermore, a high accuracy is attained in the reproducibility of the sample taking procedure. By means of the process and apparatus of the invention, it is possible without any difficulties to withdraw samples during the entire polymerization period between a 0% and a 100% conversion, even from reaction vessels wherein vinyl chloride is polymerized discontinuously with only low emulsifier concentrations of 0.5 - 1%, i.e., the thus-formed dispersions exhibit only a minor mechanical stability.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever.

EXAMPLE

In an autoclave having a capacity of 6 m$^3$ and a sampling system as shown in the drawing, vinyl chloride was discontinuously polymerized under a pressure of 9 bars and at an emulsifier concentration of 0.8%. Samples of 1 cc. were withdrawn from this autoclave below the level of the liquid by means of a pressure-proof injection syringe as shown in the drawing having a cannula of a length of 15 cm. with an internal diameter of 0.5 mm. and an outer diameter of 0.8 mm., through a diaphragm having a diameter of 13 mm. and a thickness of 4 mm. The samples were analyzed by gas chromatography; the accuracy of determining the conversion was ± 0.4%.

For comparison purposes, samples were withdrawn from the autoclave by following the gate valve method:

The sampling vessel consists of a pressure-proof container having a capacity of 10 liters, provided with a sealable opening in the lower part, as well as two closable openings in the upper part. For purposes of sample withdrawal, the sampling vessel is connected in a pressure-proof manner with the autoclave by placing the lower, closable opening in communication with the liquid-filled portion and one of the two upper openings in communication with the vapor space of the autoclave. The sampling vessel is first evacuated through the second upper opening, while the openings in communication with the autoclave are still closed. Thereafter, the opening to the vacuum pump is closed off and the connection to the vapor space of the autoclave is opened up. After pressure equalization has been attained, the communication to the liquid-filled portion of the autoclave is established, and the sampling vessel is filled up with the dispersion. Subsequently, the connections to the autoclave are closed, and the dispersions is carefully degasified under pressure through the opening preciously utilized for the evacuation of the sampling vessel. After the pressure has dropped, the dispersion can be allowed to run out of the vessel. The conversion is calculated by way of the solids concentration of the analysis. For each sample according to the gate valve method, 10 liters of dispersions was consumed.

Whereas with the aid of the method and apparatus according to this invention, a conversion of more than 95% could still be accurately determined, it was not possible by means of the gate valve method to measure conversions of about 70% or higher because the conduits conducting the dispersion became repeatly clogged up and could not be kept open.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the withdrawal of a sample from a reaction vessel under pressure and containing a dissolved and/or emulsified solid-liquid dispersion which comprises a liquified gas and which is sensitive to mechanical stress, which comprises the steps of providing a cannula and communicant connected pressure-proof injection syringe filled with an inert protective fluid; passing the cannula through an elastic pressure-proof self-sealing diaphragm in the wall of the reaction vessel and into the interior of the latter; ejecting the protective fluid from the syringe into the reaction vessel; gradually filling the syringe with a sample of the solid-liquid dispersion; sealing the syringe to maintain the captured sample therein when the cannula is withdrawn from the diaphragm; and thereafter withdrawing the cannula from the diaphragm.

2. A process according to claim 1, wherein the injection syringe is flushed after the injection into the reaction vessel of the protective fluid in the syringe, by discharging from the syringe into the reaction vessel the solid-liquid dispersion withdrawn therefrom and then withdrawing into the syringe another sample of the dispersion in the reaction vessel.

3. A process according to claim 1, wherein the cannula is inserted into the reaction vessel to a distance of 2 - 20 cm.

4. A process according to claim 1, wherein the protective fluid is water or an aqueous emulsified solution employed for the production of the dispersion in the reaction vessel.

5. A process according to claim 1, wherein the reaction vessel is provided with a sealing valve through which the cannula is passed before being passed through the diaphragm.

6. Apparatus for the withdrawal of a sample from a reaction vessel under pressure containing a dissolved and/or emulsified solid-liquid dispersion which contains liquefied gases and is sensitive to mechanical stress, and comprising a pressure-proof elastic self-sealing diaphragm; means mounting the diaphragm at an opening in the reaction vessel for sealing the same; a pressure-proof injection syringe and connected cannula filled with a protective fluid, with the cannula adapted to be manipulated to pierce the diaphragm for ejection of the protective fluid into the reaction vessel and subsequent withdrawal of a sample of the solid-liquid dispersion into the syringe; and a shut-off valve connected to the syringe to maintain the captured sample in the syringe when the cannula is withdrawn from the diaphragm.

7. Apparatus according to claim 6, wherein the surface area of the diaphragm is 0.2 - 4 cm$^2$.

8. Apparatus according to claim 6, wherein the volume of the injection syringe is 0.1 - 20 cc.

9. Apparatus according to claim 6, wherein the mounting means for the diaphragm includes a safety valve outwardly of the diaphragm and movable between an open position permitting passage of the cannula therethrough and a closed position sealing exterior communication with the diaphragm in the event of failure thereof after the cannula is removed.

10. Apparatus according to claim 9, wherein the safety valve is in the form of an apertured ball valve permitting passage of the cannula through the valve aperture in one position and sealing communication with the diaphragm in the other position.

* * * * *